United States Patent
Sakai

(10) Patent No.: US 10,067,333 B2
(45) Date of Patent: Sep. 4, 2018

(54) ENDOSCOPE HAVING IMAGE PICKUP SENSOR AND FIRST AND SECOND LIGHT BLOCKING MEMBERS

(71) Applicant: OLYMPUS CORPORATION, Tokyo (JP)

(72) Inventor: Seiji Sakai, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 140 days.

(21) Appl. No.: 15/158,752

(22) Filed: May 19, 2016

(65) Prior Publication Data
US 2016/0266373 A1    Sep. 15, 2016

Related U.S. Application Data

(63) Continuation of application No. PCT/JP2015/061636, filed on Apr. 15, 2015.

(30) Foreign Application Priority Data

May 21, 2014    (JP) .................. 2014-105495

(51) Int. Cl.
*A61B 1/04*        (2006.01)
*A61B 1/00*        (2006.01)
(Continued)

(52) U.S. Cl.
CPC ............ *G02B 23/2476* (2013.01); *A61B 1/00* (2013.01); *A61B 1/0052* (2013.01);
(Continued)

(58) Field of Classification Search
CPC ... A61B 1/00096; A61B 1/00163; A61B 1/05; G02B 23/243; G02B 23/2407; G02B 7/02; H04N 5/2254
See application file for complete search history.

(56) References Cited

U.S. PATENT DOCUMENTS 5,050,584 A * 9/1991 Matsuura ........... A61B 1/00068
                                                348/65
6,134,056 A * 10/2000 Nakamuka ............... G02B 9/04
                                                359/660
(Continued)

FOREIGN PATENT DOCUMENTS

JP    H10-146312 A    6/1998
JP    2005-070366 A    3/2005
(Continued)

OTHER PUBLICATIONS

Machine Language translation of JP 2006-094955, Apr. 2006.*
(Continued)

*Primary Examiner* — John P Leubecker
(74) *Attorney, Agent, or Firm* — Scully, Scott, Murphy & Presser, P.C.

(57) ABSTRACT

An image pickup unit includes an objective lens unit, cover glass fixed on a light receiving surface of an image pickup device, a circular optical member stuck to a front end face of the cover glass and having a diameter smaller than a diagonal line length of the cover glass, a holding frame having a circular fitting hole in which the optical member is fit from a rear, a first light blocking member disposed in a front of the optical member, and a second light blocking member disposed between a rear end face of the optical member and a front end face of the cover glass.

2 Claims, 13 Drawing Sheets

(51) Int. Cl.
- *G02B 23/24* (2006.01)
- *G02B 7/02* (2006.01)
- *G02B 13/00* (2006.01)
- *A61B 1/005* (2006.01)
- *A61B 1/05* (2006.01)
- *A61B 1/06* (2006.01)
- *H04N 5/225* (2006.01)

(52) U.S. Cl.
CPC ............ *A61B 1/00114* (2013.01); *A61B 1/04* (2013.01); *A61B 1/05* (2013.01); *A61B 1/0676* (2013.01); *G02B 7/02* (2013.01); *G02B 13/00* (2013.01); *G02B 23/24* (2013.01); *G02B 23/243* (2013.01); *G02B 23/2446* (2013.01); *H04N 5/2256* (2013.01); *H04N 2005/2255* (2013.01)

(56) References Cited

U.S. PATENT DOCUMENTS

| | | | | |
|---|---|---|---|---|
| 2009/0173875 | A1* | 7/2009 | Ichimura | A61B 1/00096 250/216 |
| 2009/0177043 | A1* | 7/2009 | Akiyama | A61B 1/00096 600/181 |
| 2009/0225198 | A1* | 9/2009 | Watanabe | G02B 15/173 348/240.3 |
| 2010/0063361 | A1* | 3/2010 | Kuchimaru | A61B 1/00096 600/168 |
| 2011/0046446 | A1* | 2/2011 | Hirayama | A61B 1/00091 600/158 |
| 2011/0267696 | A1* | 11/2011 | Tsuji | G02B 5/005 359/601 |
| 2012/0220828 | A1* | 8/2012 | Iwasaki | A61B 1/00188 600/109 |

FOREIGN PATENT DOCUMENTS

| | | | |
|---|---|---|---|
| JP | 2005070366 A | * | 3/2005 |
| JP | 2006094955 A | * | 4/2006 |
| JP | 2007-252943 A | | 10/2007 |
| JP | 2014-036799 A | | 2/2014 |
| WO | 2012/086263 A1 | | 6/2012 |

OTHER PUBLICATIONS

Extended Supplementary European Search Report dated Aug. 7, 2017 in European Patent Application No. 15 79 6750.6.
International Search Report dated Jul. 14, 2015 issued in PCT/JP2015/061636.

* cited by examiner

ENDOSCOPE HAVING IMAGE PICKUP SENSOR AND FIRST AND SECOND LIGHT BLOCKING MEMBERS

CROSS REFERENCE TO RELATED APPLICATION

This application is a continuation application of PCT/JP2015/061636 filed on Apr. 15, 2015 and claims benefit of Japanese Application No. 2014-105495 filed in Japan on May 21, 2014, the entire contents of which are incorporated herein by this reference.

BACKGROUND OF INVENTION

1. Field of the Invention

The present invention relates to an image pickup unit and an endoscope including an objective lens unit and an image pickup device.

2. Description of the Related Art

In order to observe a part where it is difficult to observe in-vivo of an organism, an inside of a structure or the like, an endoscope including, in a distal end portion of an insertion section insertable from an outside to the inside of the organism or the structure, an image pickup unit for picking up an optical image is used in, for example, a medical field and an industrial field.

For example, as disclosed in Japanese Patent Application Laid-Open Publication No. H10-146312, an image pickup unit of an endoscope includes an objective lens unit that picks up an object image and an image pickup device disposed in an image forming surface of the objective lens unit.

In the image pickup unit of the endoscope, for example, as shown in FIG. 13, a cover glass 23 for sealing a light receiving surface 22a is fixed on a light receiving surface 22a of an image pickup device 22. An optical member 24 made of a transparent member such as glass is stuck to a front surface of the cover glass 23.

The optical member 24 is fit in a fitting hole 21a formed in a holding frame 21 fixed to a not-shown objective lens unit and is fixed by an adhesive or the like. In this way, some image pickup units include a configuration in which the image pickup device 22 is fixed to, via the optical member 24, the holding frame 21 fixed to the objective lens unit.

In the image pickup unit including the optical member 24 fit in a rear end of the holding frame 21 fixed to the objective lens unit and the image pickup device 22 fixed to the optical member 24 as shown in FIG. 13, it is necessary to reduce an external shape of the optical member 24 in order to realize a reduction in size (a reduction in diameter) of the image pickup unit. If the external shape of the optical member 24 is reduced, it is possible to reduce an external shape of a rear end portion of the holding frame 21 as well.

As shown in FIG. 14, if a light blocking member 25 is disposed on a surface (a surface on an image side) behind the optical member 24, the ray L10 reflected on the side surface of the optical member 24 can be blocked.

As shown in FIG. 15, if the external shape of the optical member 24 is set the same as the cover glass 23 or larger than the cover glass 23, the side surface of the optical member 24 and a part against which the optical member 24 of the holding frame 21 is bumped can be provided away from the optical axis.

SUMMARY OF THE INVENTION

An image pickup unit according to an aspect of the present invention includes: an objective lens unit; a rectangular or square cover glass fixed on a light receiving surface, which is a front end face of an image pickup device; a circular optical member stuck to a front end face of the cover glass and having a diameter smaller than a diagonal line length of the cover glass; a holding frame fixed to the objective lens unit, and having a circular fitting hole in which the optical member is fit from a rear; a projecting section projecting toward a radial direction inner side in the holding frame; a first light blocking member disposed in a front of the optical member to block visual field external light reflecting on an inner wall surface of the projecting section and traveling to an inside of a pixel formation region of the image pickup device; and a second light blocking member disposed between a rear end face of the optical member and a front end face of the cover glass to block the visual field external light reflecting on a side surface of the optical member and having an angle toward the inside of the pixel formation region. An endoscope according to an aspect of the present invention includes the image pickup unit.

DETAILED DESCRIPTION OF THE PREFERRED EMBODIMENT(S)

A preferred mode of the present invention is explained below with reference to the drawings. Note that, in respective figures used in the following explanation, scales are differentiated for each of components in order to show the respective components in sizes recognizable on the drawings. The present invention is not limited to only quantities of the components, shapes of the components, ratios of sizes of the components, and a relative positional relation among the components described in the figures.

First Embodiment

Figure 1:
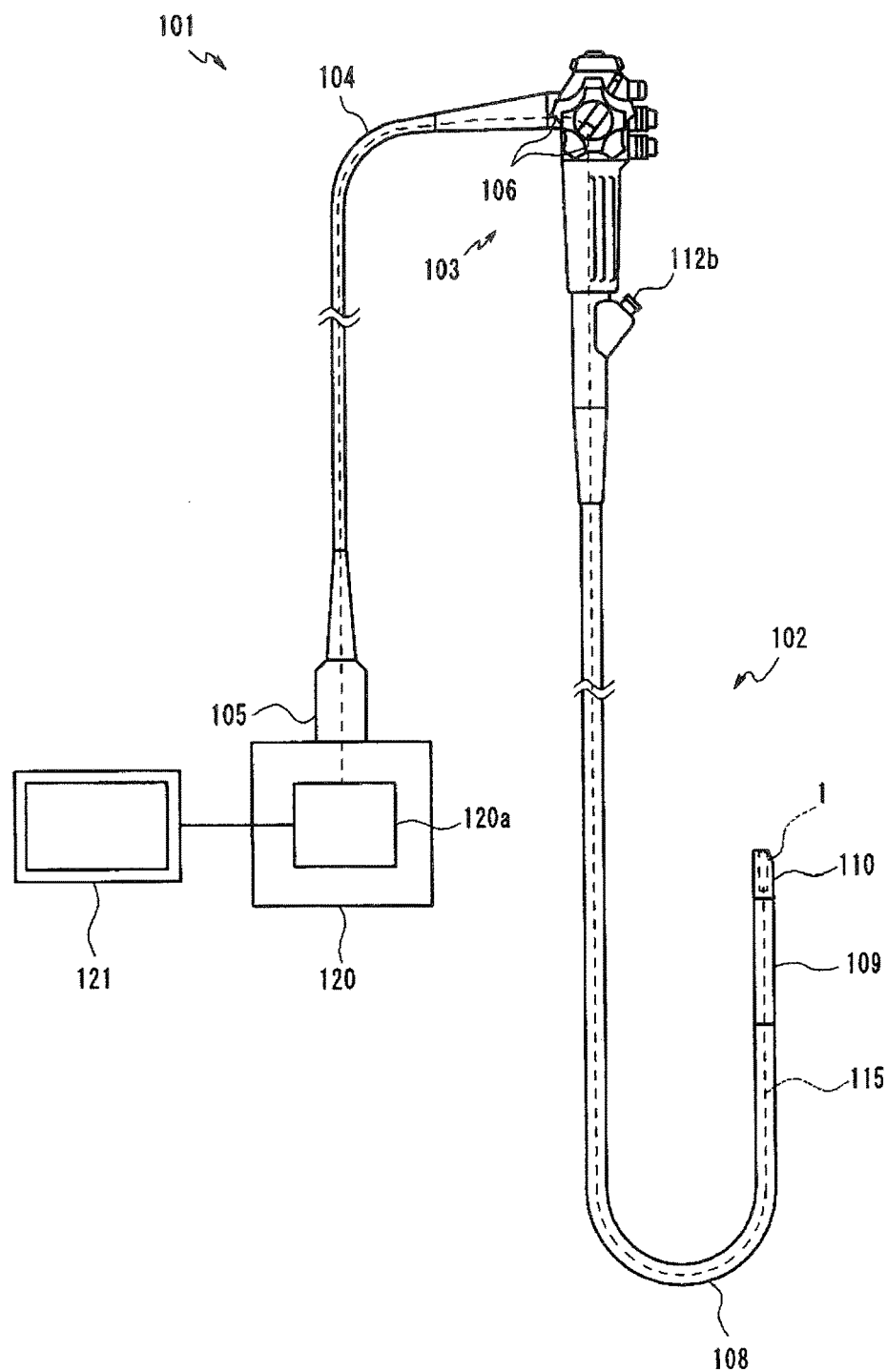
FIG. 1 is a diagram for explaining a configuration of an endoscope.

An example of an embodiment of the present invention is explained below. First, an example of a configuration of an endoscope 101 according to the present invention is explained with reference to FIG. 1. The endoscope 101 in the present embodiment includes a configuration introducible into a subject such as a human body and capable of optically picking up an image of a predetermined observation part in the subject. Note that the object into which the endoscope 101 is introduced is not limited to the human body and may be other organisms or may be an artificial object such as a machine or a structure.

The endoscope 101 in the present embodiment is mainly configured by an elongated insertion section 102 introduced into an inside of the object, an operation section 103 located at a proximal end of the insertion section 102, and a universal cord 104 extending from a side portion of the operation section 103.

The insertion section 102 is configured by concatenating a distal end portion 110 disposed at a distal end, a bendable bending section 109 disposed on a proximal end side of the distal end portion 110, and a flexible tube section 108 having flexibility disposed on a proximal end side of the bending section 109 and connected to a distal end side of the operation section 103. An image pickup unit 1 including an objective lens unit 10 and an image pickup device 2 is disposed at the distal end portion 110. Although not shown in the figure, an illumination-light emitting section that emits light for illuminating an object of the image pickup unit 1 is also provided at the distal end portion 110. Note that the endoscope 101 may be an endoscope of a form called rigid endoscope not including a part having flexibility in an insertion section.

In the operation section 103 disposed at a proximal end of the insertion section 102, an angle operation knob 106 for operating bending of the bending section 109 is provided. An endoscope connector 105 configured to be connectable to an external apparatus 120 is provided at a proximal end portion of the universal cord 104. The external apparatus 120, to which the endoscope connector 105 is connected, includes a camera control unit 120a.

In the endoscope 101, a transmission cable 115 inserted through the insertion section 102, the operation section 103, and the universal cord 104 is disposed. The transmission cable 115 is configured to electrically connect the image pickup unit 1 and the connector portion 105. The connector portion 105 is connected to the external apparatus 120, whereby the image pickup unit 1 is electrically connected to the camera control unit 120a of the external apparatus 120 via the transmission cable 115. Supply of electric power from the external apparatus 120 to the image pickup unit 1 and exchange of signals between the external apparatus 120 and the image pickup unit 1 are performed via the transmission cable 115.

The camera control unit 120a includes a configuration for generating a video based on a signal outputted from the image pickup unit 1 and outputting the video to an image display section 121. That is, in the present embodiment, an optical image picked up by the image pickup unit 1 is displayed on the image display section 121 as a video. Note that a part or all of the camera control unit 120a and the image display section 121 may be configured integrally with the endoscope 101.

Figure 2:
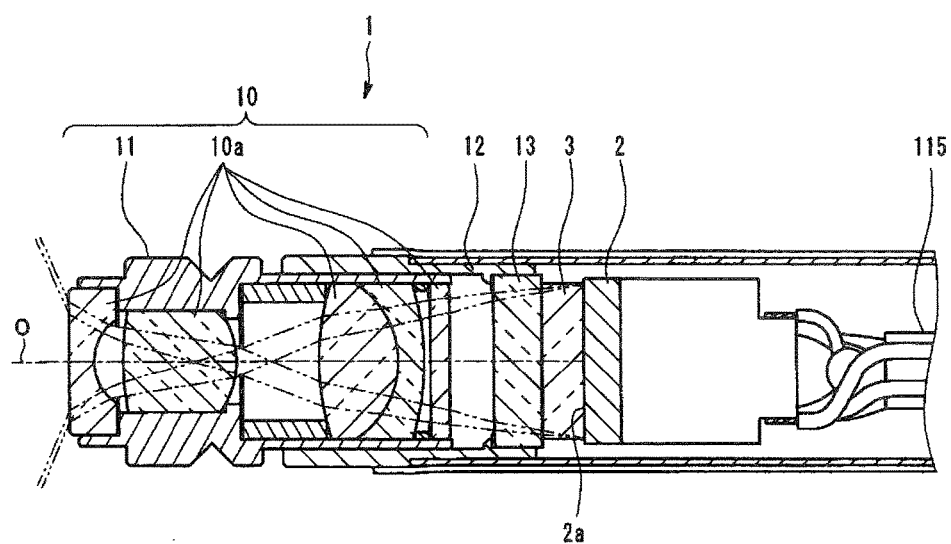
FIG. 2 is a sectional view of an image pickup unit.

A detailed configuration of the image pickup unit 1 is explained. FIG. 2 is a sectional view of the image pickup unit 1. The image pickup unit 1 includes the objective lens unit 10 and the image pickup device 2.

The objective lens unit 10 includes a plurality of optical elements such as a lens, a filter, and a diaphragm and is configured to form an object image on an image surface. In the present embodiment, as an example, the objective lens unit 10 is configured by a plurality of lenses 10a disposed on a linear optical axis O. In the following explanation, a direction toward a matter side (an object side) along the optical axis O is referred to as front and a direction toward an image side opposite to the object side is referred to as rear. Note that the objective lens unit 10 may include an optical element having a reflection surface such as a mirror or a prism. The optical axis O may bend on the reflection surface.

The plurality of lenses 10a are fixed in a cylindrical lens barrel 11. A holding frame 12 is fixed to a rear end portion of the lens barrel 11. The holding frame 12 is a cylindrical member. A front end portion of the holding frame 12 fits in the rear end portion of the lens barrel 11. A disk-like optical member 13 fits in an inside of a rear end portion of the holding frame 12. Details of the holding frame 12 and the optical member 13 are explained below.

The image pickup device 2 is, for example, a CCD, a MOS image sensor, or a CMOS image sensor. The image pickup device 2 includes a light receiving surface 2a on which a plurality of pixels including photodiodes are arrayed.

A cover glass 3 for sealing the light receiving surface 2a is stuck on the light receiving surface 2a of the image pickup device 2. The cover glass 3 is also referred to as lid glass or the like. A front surface of the cover glass 3 is bonded to a rear surface of the optical member 13 by an adhesive. That is, the image pickup device 2 is fixed to the holding frame 12 via the cover glass 3 and the optical member 13.

Figure 3:
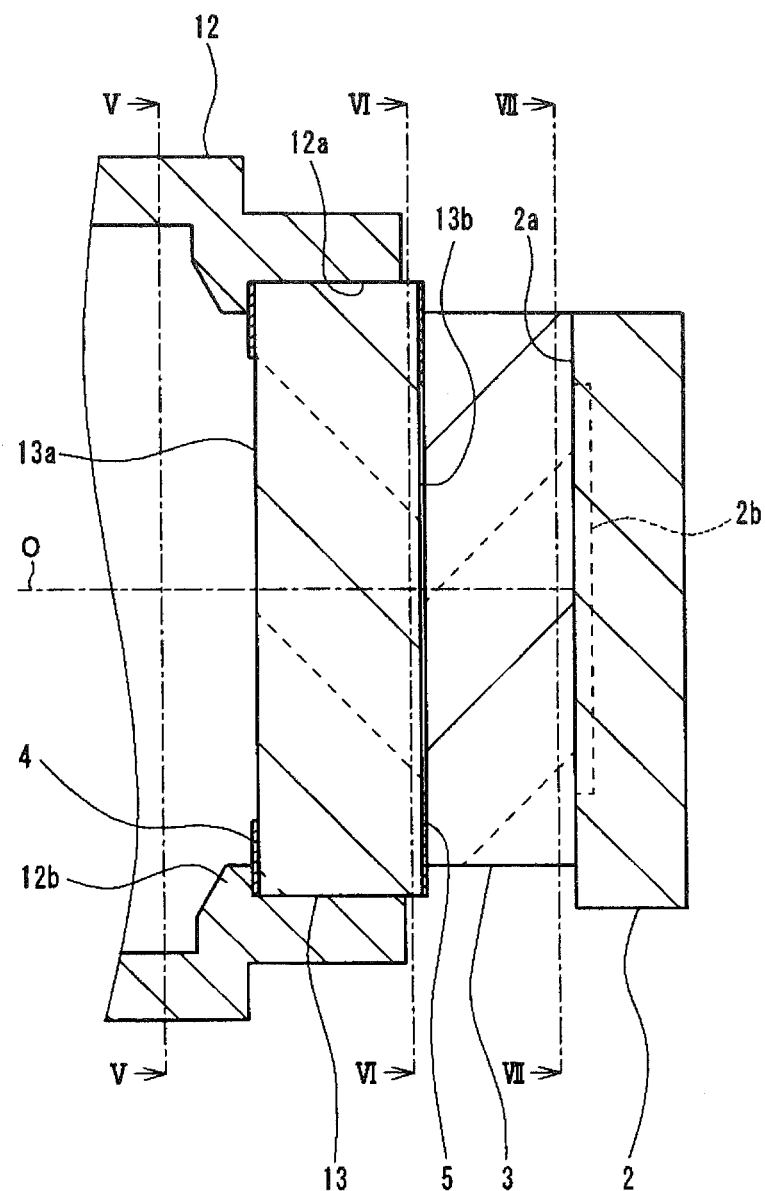
FIG. 3 is an enlarged sectional view of a rear end portion of a holding frame, an optical member, a cover glass, and an image pickup device.
Figure 4:
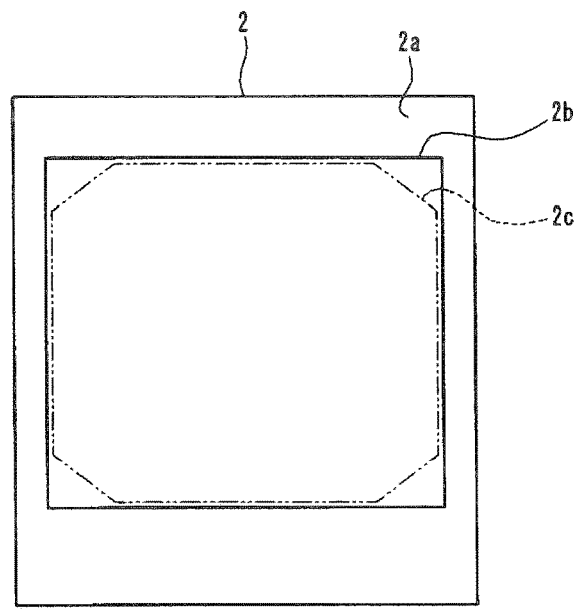
FIG. 4 is a front view of a light receiving surface of the image pickup device.
Figure 5:
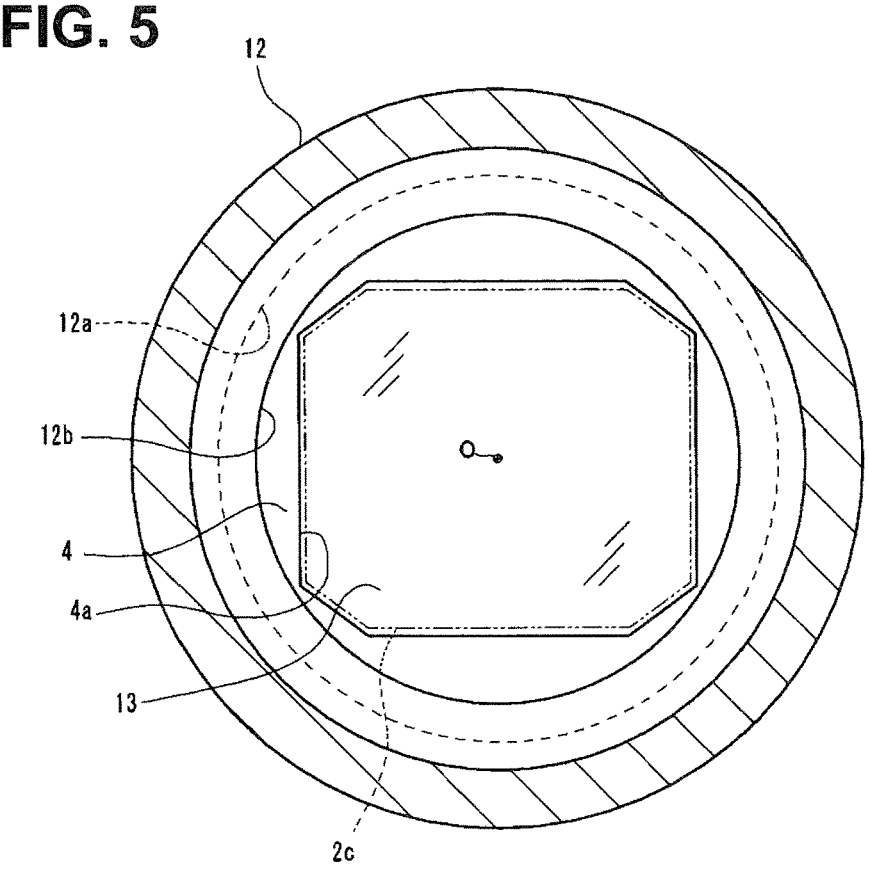
FIG. 5 is a V-V sectional view of FIG. 3.
Figure 6:
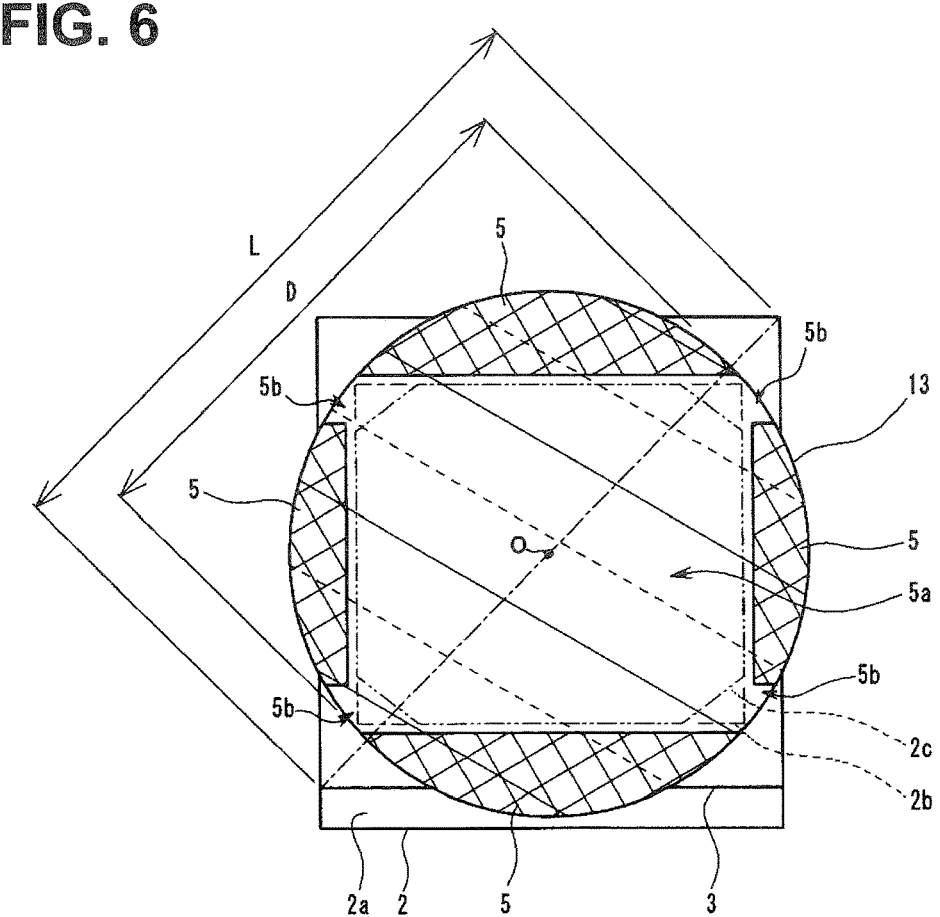
FIG. 6 is a VI-VI sectional view of FIG. 3.
Figure 7:
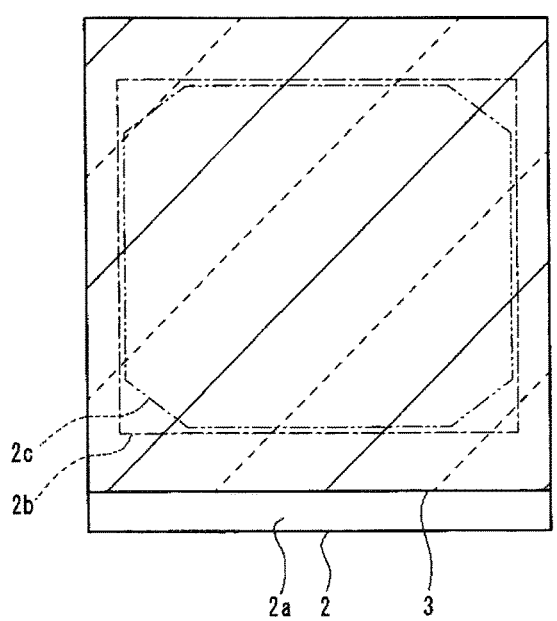
FIG. 7 is a VII-VII sectional view of FIG. 3.

FIG. 3 is an enlarged sectional view of a portion of the rear end portion of the holding frame 12, the optical member 13, the cover glass 3, and the image pickup device 2 of the image pickup unit 1. FIG. 4 is a front view of the light receiving surface 2a of the image pickup device 2. FIG. 5 is a V-V sectional view of FIG. 3. FIG. 6 is a VI-VI sectional view of FIG. 3. FIG. 7 is a VII-VII sectional view of FIG. 3.

As shown in FIG. 4, on the light receiving surface 2a of the image pickup device 2, all the pixels are formed in a pixel formation region 2b in a predetermined array. The pixel formation region 2b is, for example, rectangular or square.

In the present embodiment, the camera control unit 120a generates a video displayed on the image display section 121 using the pixels in a partial region in the pixel formation region 2b rather than generating a video displayed on the image display section 121 using all the pixels of the pixel formation region 2b of the image pickup device 2. The region including the pixels used for signal generation for generating the video is defined as display region 2c.

In the present embodiment, as an example, the display region 2c is octagonal. More specifically, the display region 2c has four outer sides parallel to an external shape of the rectangular or square pixel formation region 2b. The display region 2c has a shape obtained by cutting off, with straight lines, four corner portions of a quadrangle shape formed by the four outer sides. The image pickup device 2 is disposed such that a center of the display region 2c is located on the optical axis O. In the present embodiment, a center of the pixel formation region 2b and the center of the display region 2c coincide with each other.

Note that, in converting an optical image formed in the display region 2c into a video displayed on the image display section 121, a form may be used in which a driving mode of the image pickup device 2 is set such that the image pickup device 2 outputs only signals from the pixels located in the display region 2c. Alternatively, a form may be used in which, after signals outputted form all the pixels of the image pickup device 2 are read out, a video in a region equivalent to the display region 2c may be cutout by image processing. The center of the pixel formation region 2b and the center of the display region 2c do not have to coincide with each other. An aspect ratio of the pixel formation region 2b and an aspect ratio of the display region 2c do not have to be the same.

As shown in FIG. 3 and FIG. 7, the cover glass 3 is fixed on the light receiving surface 2a of the image pickup device 2. The cover glass 3 is a member that seals the pixel formation region 2b. The cover glass 3 is a flat plate that is rectangular or square when viewed from a direction parallel to the optical axis O. The cover glass 3 has an external shape larger than the pixel formation region 2b when viewed from the direction parallel to the optical axis O.

As shown in FIG. 7, the cover glass 3 is disposed such that four outer sides of the cover glass 3 are parallel to an external shape of the pixel formation region 2b and the cover glass 3 covers the entire pixel formation region 2b when viewed from the direction parallel to the optical axis O. A center of the cover glass 3 is located on the optical axis O.

As shown in FIG. 3 and FIG. 6, the optical member 13 is fixed on a surface on an opposite side of the image pickup device 2 of the cover glass 3, that is, the front surface of the cover glass 3. The optical member 13 is a flat plate made of a transparent material such as glass and circular when viewed from the direction parallel to the optical axis O. The disk-like optical member 13 is disposed such that a center is located on the optical axis O.

As shown in FIG. 6, a diameter D of the optical member 13 is smaller than a diagonal line length L of the rectangular or square cover glass 3. The diameter D of the optical member 13 is set to a value for covering the entire display region 2c with the optical member 13 when viewed from the direction parallel to the optical axis O. In this way, the diameter D of the circular optical member 13 is set smaller than the diagonal line length L of the rectangular or square cover glass 3. Consequently, it is possible to reduce projection of the optical member 13 from the external shape of the cover glass 3. It is possible to realize a reduction in size of the image pickup unit 1.

As shown in FIG. 3 and FIG. 5, a fitting hole 12a is formed at the rear end portion of the holding frame 12. A rear end of the cylindrical holding frame 12 has a shape cut off by a plane orthogonal to the optical axis O.

The fitting hole 12a is a circular hole centering on the optical axis O. The fitting hole 12a has an inner diameter in which the disk-like optical member 13 fits. The optical member 13 is inserted from the rear to the front in the fitting hole 12a and fixed by an adhesive.

A projecting section 12b projecting toward a radial direction inner side of the fitting hole 12a is provided on an inner wall surface of the fitting hole 12a. The projecting section 12b is a part for positioning the optical member 13 in the direction parallel to the optical axis O. In the present embodiment, as shown in FIG. 5, the projecting section 12b is provided over an entire circumferential direction of the inner wall surface of the fitting hole 12a.

The projecting section 12b is provided at a predetermined distance from the rear end of the holding frame 12 toward the front in parallel to the optical axis O. A distance between the rear end of the holding frame 12 and a rear end of the projecting section 12b is shorter than thickness of the optical member 13.

In the image pickup unit 1 in the present embodiment, as shown in FIG. 3, a first light blocking member 4 and a second light blocking member 5 are disposed in contact with a front end face 13a of the optical member 13 and a rear end face 13b of the optical member 13.

The first light blocking member 4 and the second light blocking member 5 are members for blocking visual field external light made incident on the objective lens unit 10 from an outside of a visual field of the image pickup unit 1. The visual field external light refers to a ray other than a ray that forms an image in the display region 2c among rays that reach the rear end portion of the holding frame 12 passing through the objective lens unit 10. The first light blocking member 4 and the second light blocking member 5 are thin plate-like or thin film-like members made of a material that does not transmit light such as metal or resin.

In the present embodiment, as an example, the first light blocking member 4 is a thin plate-like member held between the rear end of the projecting section 12b and the front end face 13a of the optical member 13 in the fitting hole 12a. Note that the first light blocking member 4 may be a thin film formed on the front end face 13a of the optical member 13 by vapor deposition or the like.

As shown in FIG. 5, the first light blocking member 4 includes an opening section 4a, which is a hole through which the optical axis O pierces. The opening section 4a has an octagonal shape similar to a shape of the display region 2c when viewed from the direction parallel to the optical axis O and is provided such that respective sides are parallel to respective sides of the display region 2c. In FIG. 5, an external shape of the display region 2c is indicated by an alternate long and two short dashes line. A ray passing through the objective lens unit 10 and forming an image in the display region 2c passes through the opening section 4a.

Note that a relation between sizes of the display region 2c and the opening section 4a is appropriately decided according to an angle of the ray that forms an image in the display region 2c passing through the objective lens unit 10. Therefore, in the present embodiment shown in the figure, the opening section 4a is larger than the display region 2c. However, the opening section 4a may have size same as the size of the display region 2c or may be smaller than the display region 2c.

In the present embodiment, as an example, the second light blocking member 5 is a thin film made of metal formed on the rear end face 13b of the optical member 13. The second light blocking member 5 is formed by, for example, a vapor deposition method. Note that the second light blocking member 5 may be a thin plate-like member.

In FIG. 6, a shape of the second light blocking member 5 viewed from the direction parallel to the optical axis O is indicated by hatching of half-tone dot meshing.

As shown in FIG. 6, the second light blocking member 5 is an outer edge portion of the rear end face 13b of the optical member 13 and is provided in a region where the second light blocking member 5 does not hinder the ray that forms an image in the display region 2c passing through the objective lens unit 10. In other word, the second light blocking member 5 includes an opening section 5a through which the optical axis O pierces. The ray that forms an image in the display region 2c passing through the objective lens unit 10 passes through the opening section 5a.

Note that, in FIG. 6, the external shape of the display region 2c is indicated by an alternate long and short dashes line. In FIG. 6, four corner portions of the rectangular or square pixel formation region 2b are indicated by alternate long and short dash lines.

The second light blocking member 5 includes the opening section 5a having a shape similar to a rectangular or a square shape formed by four outer sides parallel to the external shape of the pixel formation region 2b in the outer sides of the display region 2c. Note that a relation between sizes of the display region 2c and the opening section 5a is appropriately decided according to an angle of the ray that forms an image in the display region 2c passing through the objective lens unit 10. Therefore, in the present embodiment shown in the figure, the opening section 5a is larger than the display region 2c. However, the opening section 5a may have size same as the size of the display region 2c or may be smaller than the display region 2c.

In the present embodiment, as shown in FIG. 6, the second light blocking member 5 includes cutout sections 5b at four corner portions of the opening section 5a. The cutout sections 5b are regions where the second light blocking member 5 is not formed and transmit light. The cutout sections 5b are provided in regions overlapping the four corner portions of the pixel formation region 2b when viewed from the direction parallel to the optical axis O.

That is, when the optical member 13, the cover glass 3, and the image pickup device 2 are viewed from the front in parallel to the optical axis O, the four corner portions of the pixel formation region 2b are seen through the cutout sections 5b. In this way, the cutout sections 5b are provided in the regions overlapping the four corner portions of the pixel formation region 2b when viewed from the front of the second light blocking member 5. Consequently, when the rear end face 13b of the optical member 13 on which the second light blocking member 5 is formed and a front end face of the cover glass 3 fixed to the image pickup device 2 are stuck together, it is possible to easily position the rear end face 13b and the front end face on the basis of the external shape of the pixel formation region 2b.

As explained above, the image pickup unit 1 in the present embodiment includes, the objective lens unit 10, the rectangular or square cover glass 3 fixed on the light receiving surface 2a, which is the front end face of the image pickup device 2, the circular optical member 13 stuck to the front end face of the cover glass 3 and having a diameter smaller than the diagonal line length of the cover glass 3, the holding frame 12 fixed to the objective lens unit 10, and having a circular fitting hole 12a in which the optical member 13 is fit from a rear, the projecting section 12b projecting toward the radial direction inner side in the holding frame 12, the first light blocking member 4 disposed between the projecting section 12b and the front end face 13a of the optical member 13 to block the visual field external light, and the second light blocking member 5 disposed between the rear end face 13b of the optical member 13 and the cover glass 3 to block the visual field external light.

Figure 8:
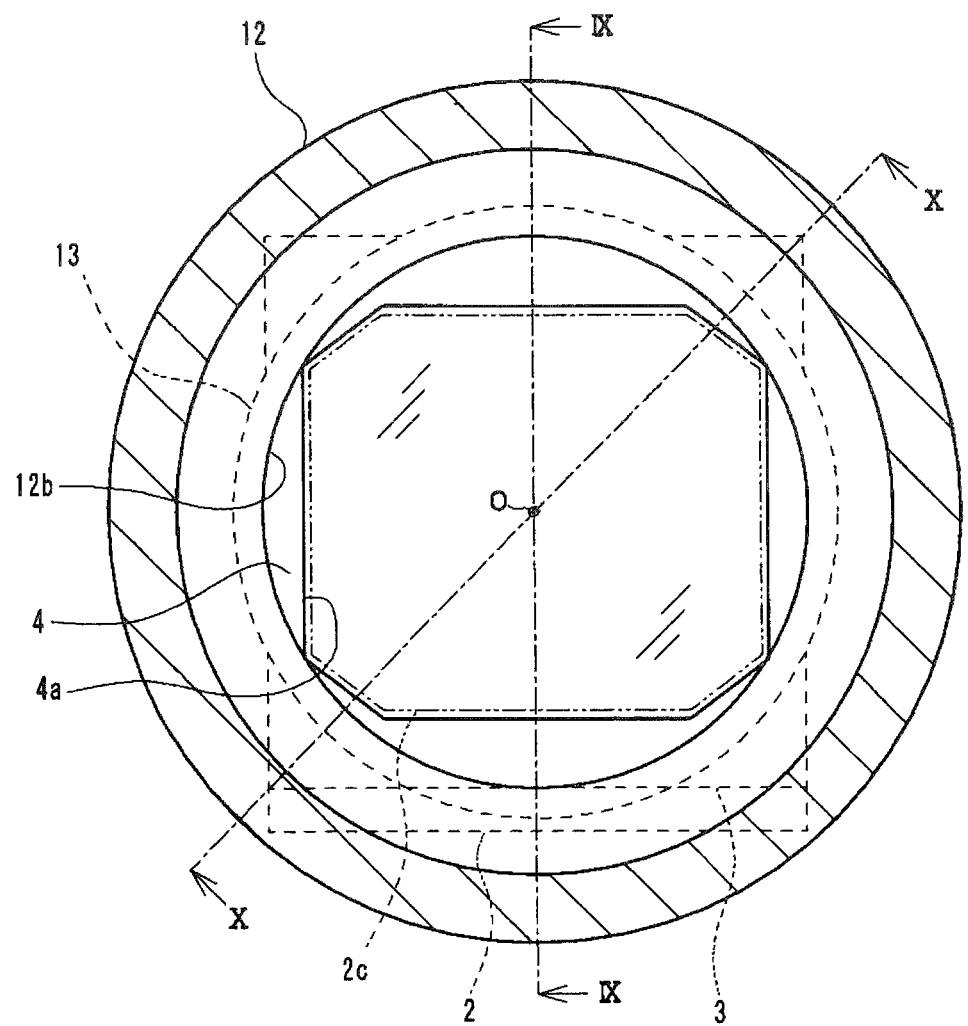
FIG. 8 is a diagram showing respective external shapes of the rear end portion of the holding frame, the optical member, the cover glass, and the image pickup device viewed from a front.

Action of the first light blocking member 4 and the second light blocking member 5 is explained below. FIG. 8 is a diagram showing respective external shapes of the rear end portion of the holding frame 12, the optical member 13, the cover glass 3, and the image pickup device 2 viewed from the front in parallel to the optical axis O.

In the image pickup unit 1 in the present embodiment, a diameter of the circular optical member 13 is smaller than the diagonal line length of the rectangular or square cover glass 3. Therefore, when viewed from the front in parallel to the optical axis O, four corner portions of the cover glass 3 project further toward a radial direction outer side (farther from the optical axis O) than an external shape of the optical member 13. In other parts, when viewed from the front in parallel to the optical axis O, outer sides of the cover glass 3 are located further on a radial direction inner side than the external shape of the optical member 13.

Figure 9:
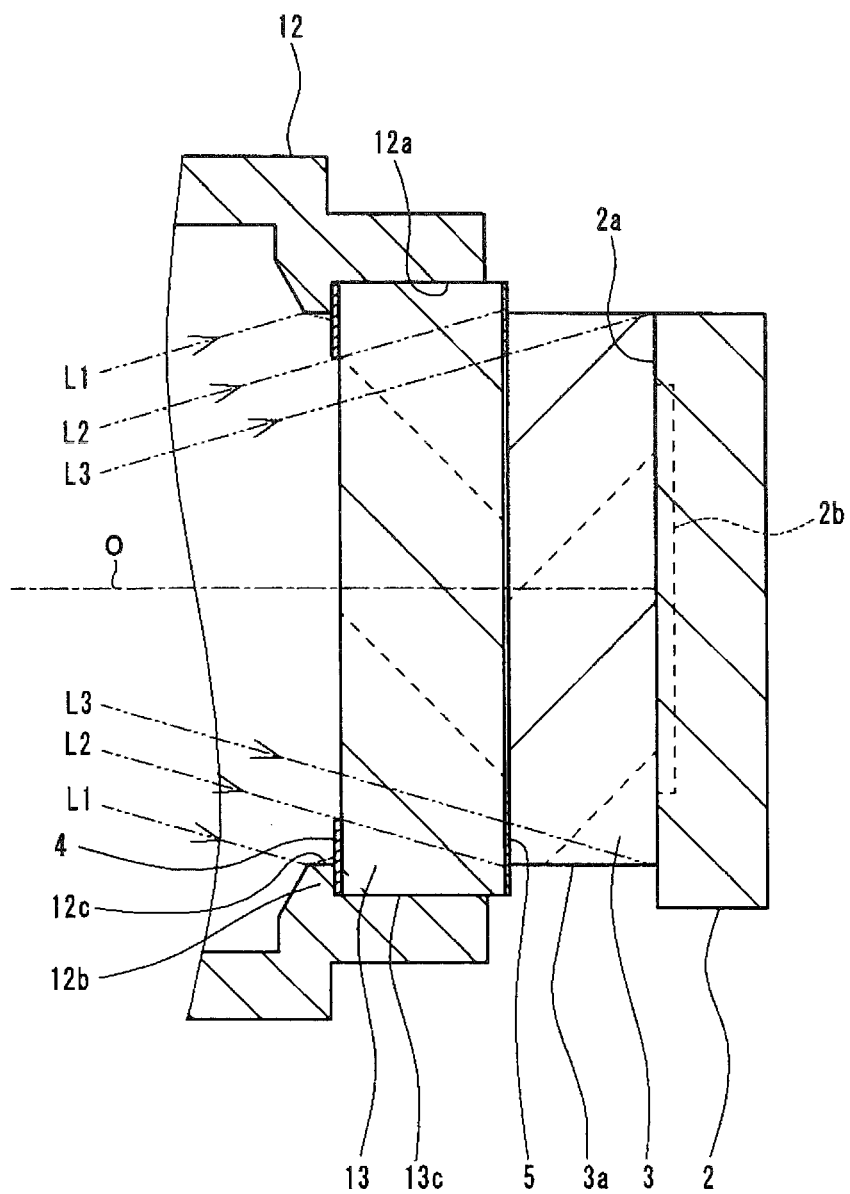
FIG. 9 is a IX-IX sectional view of FIG. 8.
Figure 10:
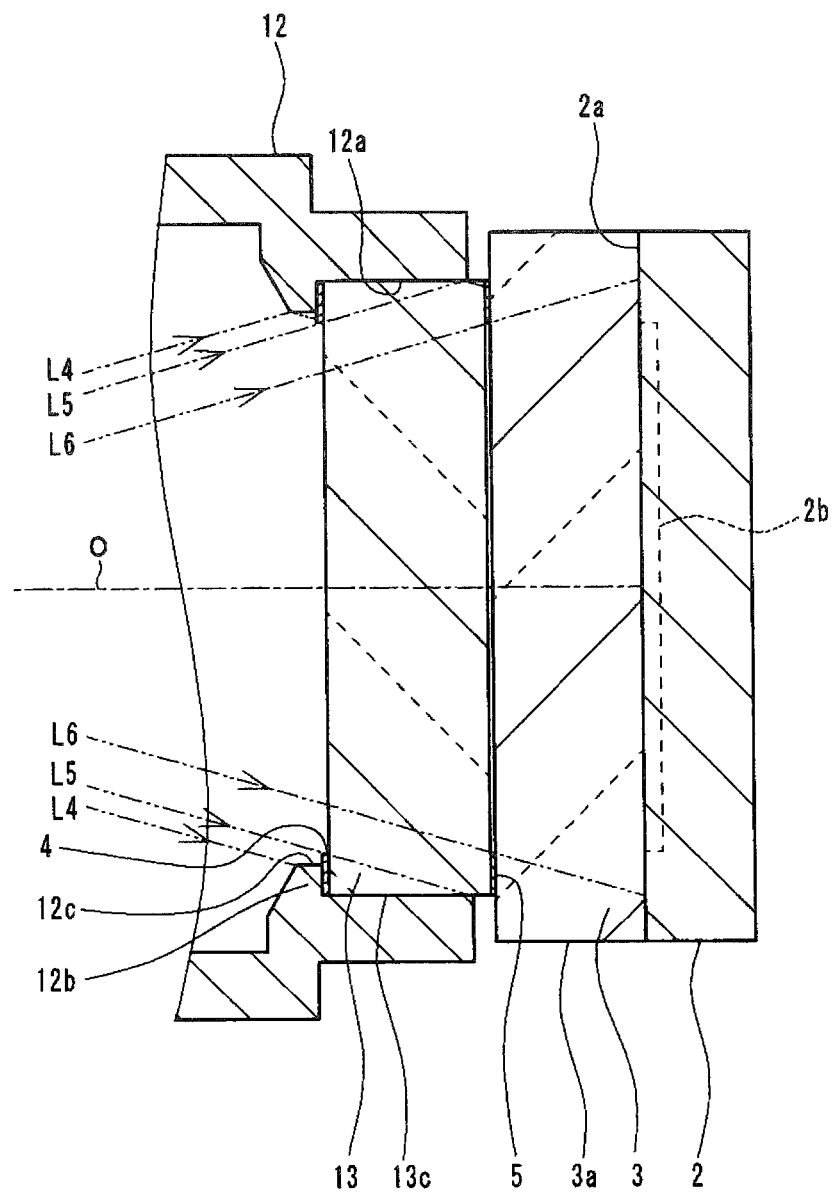
FIG. 10 is a X-X sectional view of FIG. 8.

FIG. 9 is a IX-IX sectional view in FIG. 8 and is a cross section taken along a plane including the optical axis O. FIG. 9 shows a part where the cover glass 3 is located further on the radial direction inner side than the external shape of the optical member 13. FIG. 10 is a X-X sectional view in FIG. 8 and is a cross section taken along the plane including the optical axis O. FIG. 10 shows a part where the cover glass 3 projects further toward the radial direction outer side than the external shape of the optical member 13.

In order to block harmful lights such as flares adversely affecting an image in the image pickup unit 1, among visual field external lights that reach the rear end portion of the holding frame 12 passing through the objective lens unit 10, it is necessary to block light reflecting on an inner wall surface 12c of the projecting section 12b, a side surface 13c of the optical member 13, and a side surface 3a of the cover glass 3 and reaching the display region 2c.

In the present embodiment, as shown as line segments L1 and L4 of alternate long and short two dashes lines in FIG. 9 and FIG. 10, visual field external lights reflecting toward the inside of the display region 2c on the inner wall surface 12c of the projecting section 12b are blocked by the first light blocking member 4 disposed in the front of the optical member 13.

As shown as line segments L2 and L5 of alternate long and two short dashes lines in FIG. 9 and FIG. 10, parts of visual field external lights having angles of incidence on the side surface 13c of the optical member 13 are blocked by the first light blocking member 4. Visual field external lights made incident on the side surface 13c of the optical member 13 without being blocked by the first light blocking member 4 and reflecting toward the inside of the display region 2c are blocked by the second light blocking member 5 disposed in the rear of the optical member 13.

As shown as line segments L3 and L6 of alternate long and two short dashes lines in FIG. 9 and FIG. 10, visual field external lights having angles of incidence on the side surface 3a of the cover glass 3 are not made incident on the display region 2c.

As explained above, in the present embodiment, among the visual field external lights that reaches the rear end portion of the holding frame 12 passing through the objective lens unit 10, all harmful lights such as flares adversely affecting an image can be blocked by the first light blocking member 4 and the second light blocking member 5.

As explained above, the image pickup unit 1 and the endoscope 101 in the present embodiment can achieve both of a reduction in size by a reduction in the diameter of the circular optical member 13 and suppression of flares.

Note that, in the present embodiment explained above, the projecting section 12b is provided over the entire circumferential direction of the inner wall surface of the fitting hole 12a to form a circular opening for transmitting a ray emitted from the objective lens unit 10. However, as shown as a modification in FIG. 11, the projecting section 12b may form an opening having a shape different from the circular shape.

Figure 11:
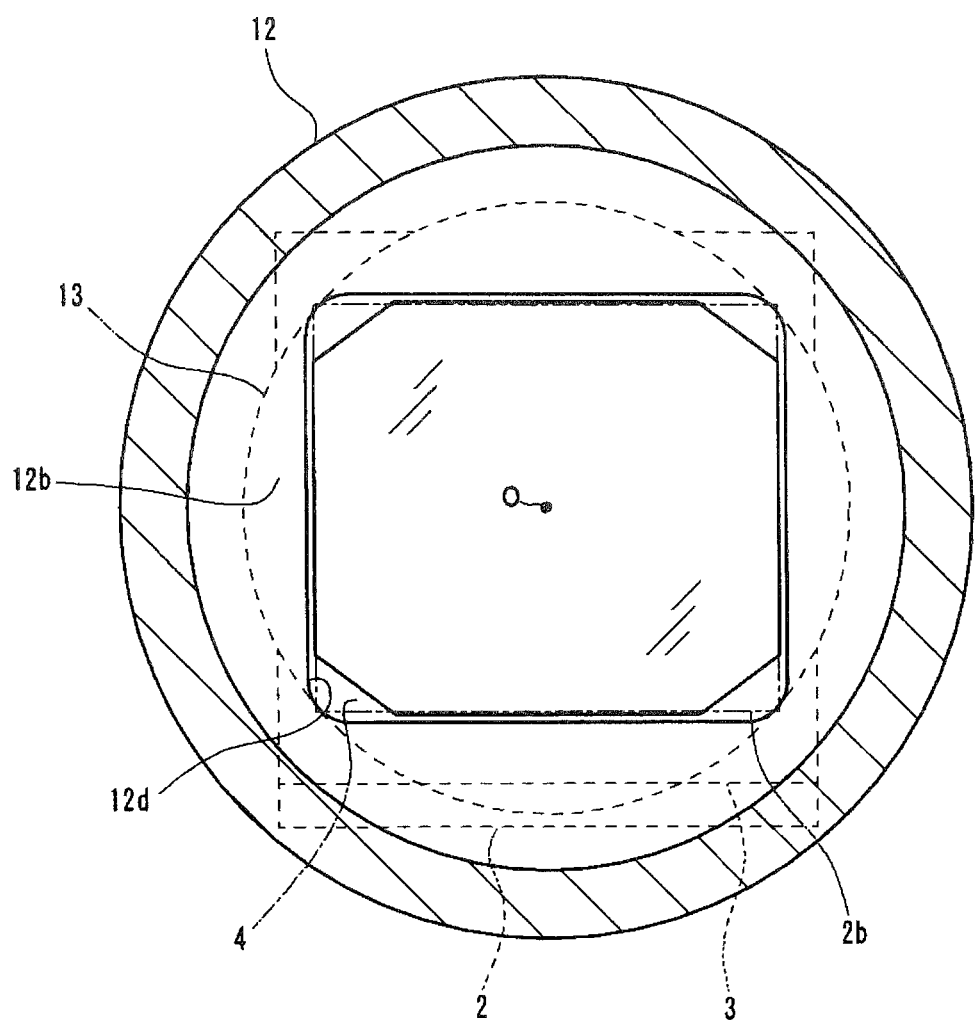
FIG. 11 is a diagram showing a modification of a protrusion section.

In the modification shown in FIG. 11, an opening 12d formed in the fitting hole 12a by the projecting section 12b has a rectangular shape or a square shape formed by four sides parallel to the external shape of the pixel formation region 2b. The rectangular or square opening 12d is inscribed with the inner wall surface of the fitting hole 12a. Therefore, the projecting section 12b is divided in the circumferential direction at four corner portions of the opening 12d. In other words, when viewed from the direction parallel to the optical axis O, portions of the projecting section 12b overlapping vicinities of the four corners of the pixel formation region 2b are cut out.

In such a modification, at the four corner portions of the pixel formation regions 2b, which are positions with large image height, it is possible to prevent occurrence of flares due to visual field external lights reflected on the inner wall surface 12c of the projecting section 12b.

Second Embodiment

A second embodiment of the present invention is explained below. Only differences from the first embodiment are explained below. Components same as the components in the first embodiment are denoted by the same reference numerals and signs. Explanation of the components is omitted as appropriate.

Figure 12:
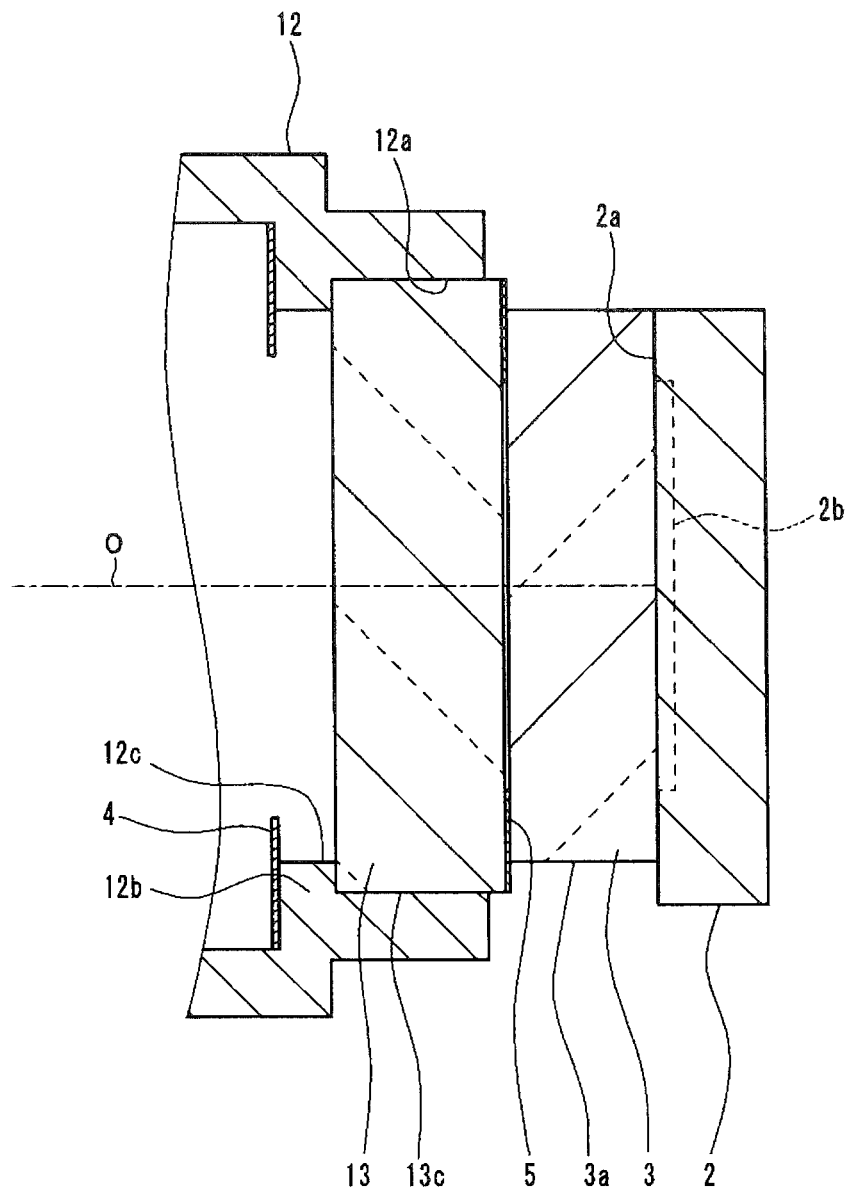
FIG. 12 is a sectional view of an image pickup unit of a second embodiment.
Figure 13:
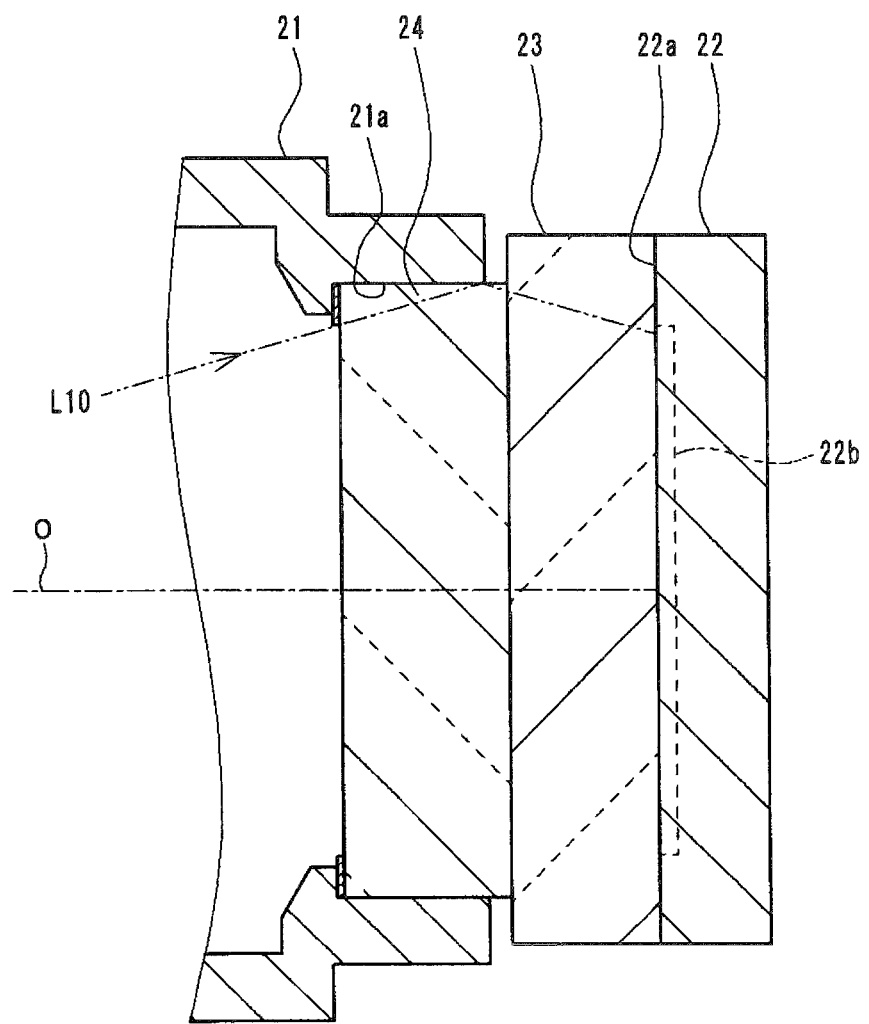
FIG. 13 is a sectional view for explaining a conventional image pickup unit.
Figure 14:
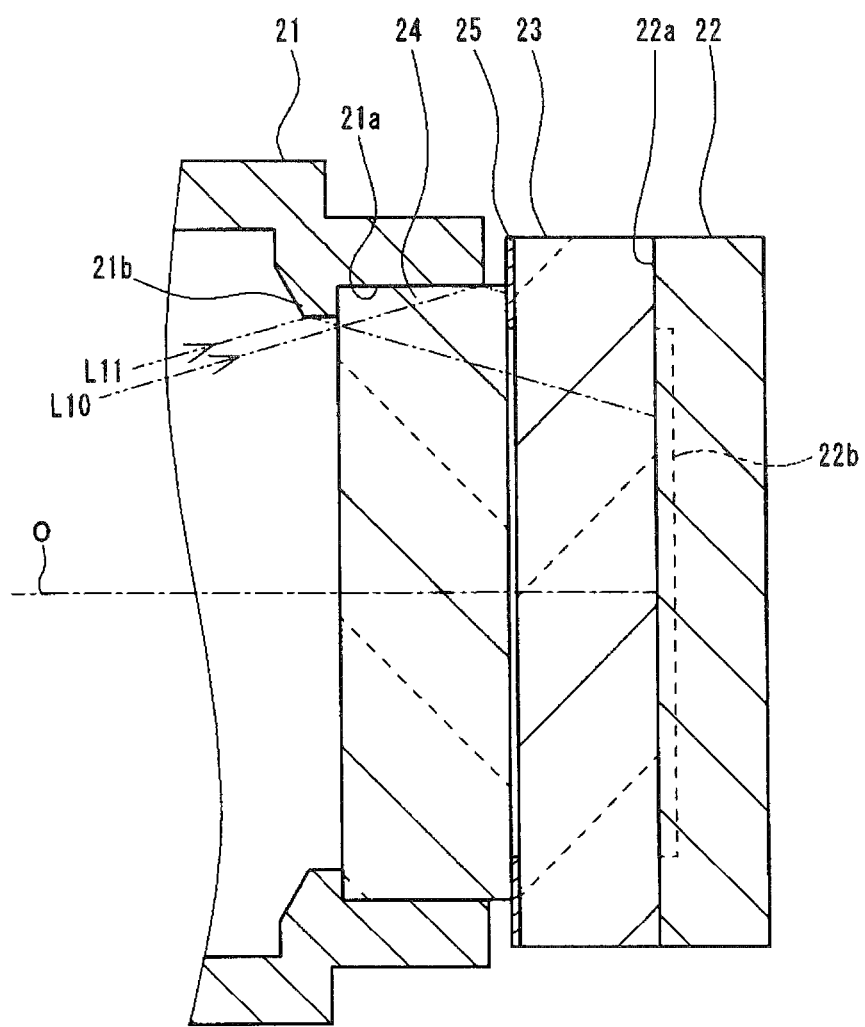
FIG. 14 is a sectional view for explaining the conventional image pickup unit.
Figure 15:
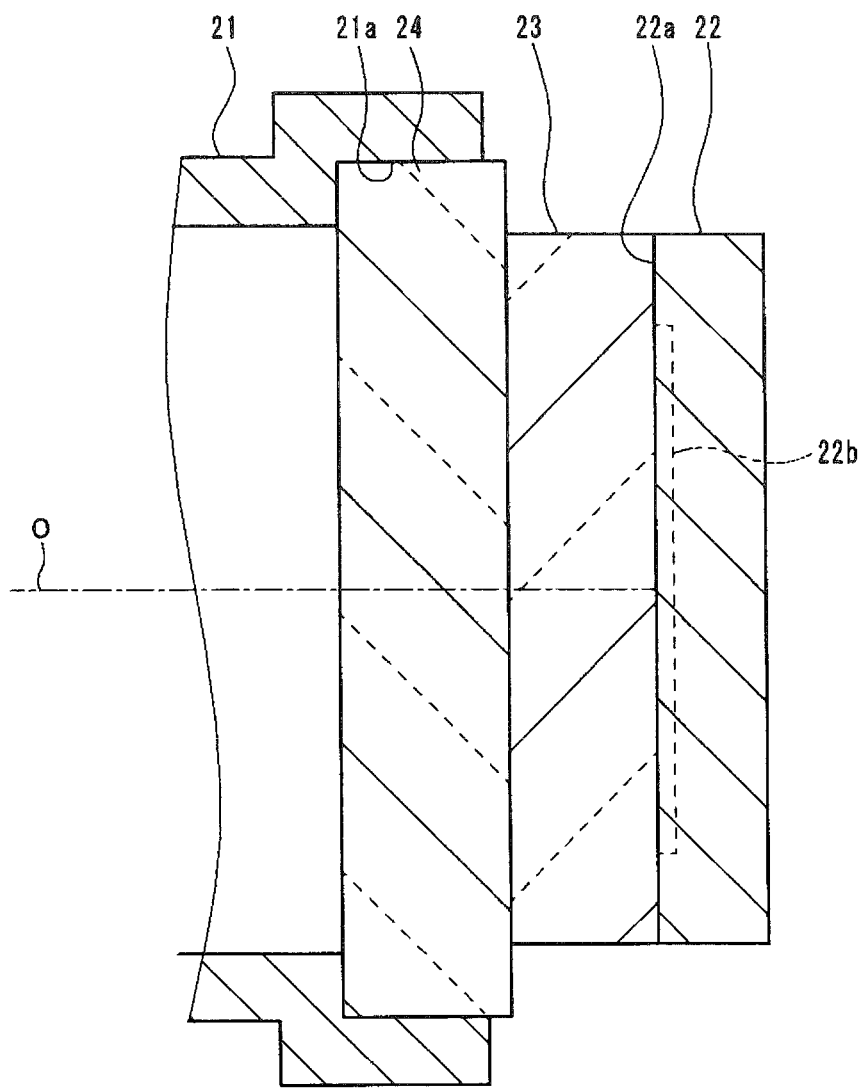
FIG. 15 is a sectional view for explaining the conventional image pickup unit.

The image pickup unit 1 in the present embodiment is different from the first embodiment in a disposition part of the first light blocking member 4. As shown in FIG. 12, the first light blocking member 4 of the present embodiment is in contact with a front end face of a protrusion section 12 and fixed.

By disposing the first light blocking member 4 on the front end face of the protrusion section 12 as in the present embodiment, visual field external lights having angles of incidence on the inner wall surface 12c of the protrusion section 12 can be blocked by the first light blocking member 4.

As in the first embodiment, the first light blocking member 4 blocks parts of visual field external lights having angles of incidence on the side surface 13c of the optical member 13. A disposition part of the second light blocking member 5 is the same as the disposition part in the first embodiment. Therefore, the second light blocking member 5 blocks visual field external lights made incident on the side surface 13c of the optical member 13 without being blocked by the first light blocking member 4 and reflecting toward the inside of the display region 2c. Visual field external lights having angles of incidence on the side surface 3a of the cover glass 3 are not made incident on the display region 2c.

As explained above, in the present embodiment, as in the first embodiment, among the visual field external lights that reaches the rear end portion of the holding frame 12 passing through the objective lens unit 10, all harmful lights such as flares adversely affecting an image can be blocked by the first light blocking member 4 and the second light blocking member 5.

Therefore, the image pickup unit 1 and the endoscope 101 in the present embodiment can achieve both of a reduction in size by a reduction in the diameter of the circular optical member 13 and suppression of flares.

The present invention is not limited to the embodiments explained above and can be changed as appropriate in a range not departing from the spirit or the idea of the invention read from claims and the entire specification. Image pickup units and endoscopes involving such changes are also included in the technical scope of the present invention.

What is claimed is:

1. An endoscope comprising:
an objective lens unit;
an image pickup sensor configured to generate an image signal;
a rectangular or square cover glass fixed on a light receiving surface, which is a front end face of the image pickup sensor;
a circular optical member stuck to a front end face of the cover glass and having a diameter smaller than a diagonal line length of the cover glass;
a holding frame fixed to the objective lens unit, and having a circular fitting hole in which the optical member is fit from a rear;
a projecting section projecting toward a radial direction inner side in the holding frame;
a first light blocking member disposed in a front of the optical member to block visual field external light reflecting on an inner wall surface of the projecting section and traveling to an inside of a pixel formation region of the image pickup sensor;
a second light blocking member disposed between a rear end face of the optical member and a front end face of the cover glass to block the visual field external light reflecting on a side surface of the optical member and having an angle toward the inside of the pixel formation region;
a controller configured to perform display based on the image signal generated by the image pickup sensor, wherein
the image pickup sensor includes a pixel formation region for receiving an optical image, the pixel formation region having a rectangular shape,
a display region configured to be displayed on a display apparatus is defined in the pixel formation region, the display region having an octagonal shape,
the controller is configured to generate a display signal corresponding to the display region and output the generated display signal to the display apparatus,
the first light blocking member includes a first opening through which light from the objective lens unit passes, the first opening having an octagonal shape and having a same size as the display region,
the second light blocking member includes a second opening through which light from the first opening passes, the second opening having a rectangular shape and having a same size as the pixel formation region of the image pickup sensor, and
four cutout sections are formed corresponding to four corners of the second opening, and corner portions of the pixel formation region are visible through the cutout sections.

2. The endoscope according to claim 1, wherein the second light blocking member is made of a thin film vapor-deposited on the rear end face of the optical member.

* * * * *